United States Patent
Wang et al.

(10) Patent No.: US 9,637,437 B2
(45) Date of Patent: May 2, 2017

(54) PROCESS FOR THE PREPARATION OF BENZENE DERIVATIVES FROM FURAN DERIVATIVES

(71) Applicant: Furanix Technologies B.V., Amsterdam (NL)

(72) Inventors: Bing Wang, Amsterdam (NL); Gerardus Johannes Maria Gruter, Amsterdam (NL); Matheus Adrianus Dam, Amsterdam (NL); Robert Michael Kriegel, Decatur, GA (US)

(73) Assignees: FURANIX TECHNOLOGIES B.V., Amsterdam (NL); THE COCA-COLA COMPANY, Atlanta, GA (US)

( * ) Notice: Subject to any disclaimer, the term of this patent is extended or adjusted under 35 U.S.C. 154(b) by 0 days.

(21) Appl. No.: 14/435,470

(22) PCT Filed: Oct. 22, 2013

(86) PCT No.: PCT/NL2013/050740
§ 371 (c)(1),
(2) Date: Apr. 14, 2015

(87) PCT Pub. No.: WO2014/065657
PCT Pub. Date: May 1, 2014

(65) Prior Publication Data
US 2016/0137579 A1    May 19, 2016

Related U.S. Application Data

(60) Provisional application No. 61/716,788, filed on Oct. 22, 2012.

(30) Foreign Application Priority Data

Oct. 22, 2012 (NL) .......................... 2009674

(51) Int. Cl.
C07C 51/25 (2006.01)
C07C 51/50 (2006.01)
(Continued)

(52) U.S. Cl.
CPC .............. C07C 51/25 (2013.01); C07C 2/865 (2013.01); C07C 51/265 (2013.01);
(Continued)

(58) Field of Classification Search
CPC ......... C07C 51/25; C07C 51/50; C07C 2/865; C07C 2523/44; C07C 2523/89;
(Continued)

(56) References Cited

U.S. PATENT DOCUMENTS 4,138,354 A   2/1979  Sochol et al.
4,230,882 A   10/1980 Seko et al.
(Continued)

FOREIGN PATENT DOCUMENTS

WO    2007104515 A1   9/2007
WO    2009064515 A1   5/2009
(Continued)

OTHER PUBLICATIONS

Cheng, Y.T. et al.: "Production of targeted aromatics by using Diels-Alder classes of reactions with furans and olefins over ZSM-5", Green Chemistry, vol. 14, No. 11, Aug. 21, 2012, pp. 3114-3125.
Williams, C.L. et al.: "Cycloaddition of Biomass-Derived Furans for Catalytic Production of Renewable p-Xylene", ACS Catalysis, vol. 2, No. 6, Apr. 18, 2012, pp. 935-939.

*Primary Examiner* — Shailendra Kumar
(74) *Attorney, Agent, or Firm* — Hoffmann & Baron, LLP

(57) ABSTRACT

Benzene derivatives of the formula (I);

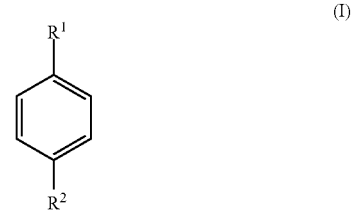

(I)

wherein $R^1$ and $R^2$, are the same or different and independently are selected from the group consisting of hydrogen, alkyl, aralkyl, —CHO, —$CH_2OR^3$, —$CH(OR^4)(OR^5)$ and —$COOR^6$, wherein $R^3$, $R^4$ and $R^5$ are the same or different and are selected from hydrogen, alkyl, aryl, alkaryl, aralkyl, alkylcarbonyl or arylcarbonyl, or wherein $R^4$ and $R^5$ together form an alkylene group and wherein $R^6$ is selected from hydrogen, alkyl and aryl, are prepared in a process, which comprises:

reacting a furan derivative of formula (II):

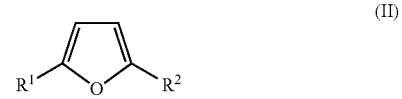

(II)

wherein $R^1$ and $R^2$ have the meanings above, with ethylene under cycloaddition reaction conditions in the presence of an acid solvent to produce the benzene derivative, wherein the acid solvent is a carboxylic acid and is present in a weight ratio acid solvent to furan derivative from 1:1 to 250:1.

34 Claims, No Drawings

(51) Int. Cl.
    *C07C 2/86*     (2006.01)
    *C07C 51/265*     (2006.01)
    *C07C 51/353*     (2006.01)

(52) U.S. Cl.
    CPC ............ *C07C 51/353* (2013.01); *C07C 51/50* (2013.01); *C07C 2521/08* (2013.01); *C07C 2521/18* (2013.01); *C07C 2523/44* (2013.01); *C07C 2523/745* (2013.01); *C07C 2523/89* (2013.01); *Y02P 20/582* (2015.11)

(58) Field of Classification Search
    CPC ............ C07C 2521/18; C07C 2521/08; C07C 51/265; C07C 51/353; C07C 2523/745; Y02P 20/582
    See application file for complete search history.

(56) References Cited

U.S. PATENT DOCUMENTS 7,385,081 B1     6/2008   Gong
9,260,359 B2 *   2/2016   Masuno .................. C07C 2/862

FOREIGN PATENT DOCUMENTS

WO     2010151346 A1     12/2010
WO     2013040514 A1     3/2013

\* cited by examiner

PROCESS FOR THE PREPARATION OF BENZENE DERIVATIVES FROM FURAN DERIVATIVES

CROSS-REFERENCE TO RELATED APPLICATIONS

This application is the National Stage of International Application No. PCT/NL2013/050740 filed Oct. 22, 2013, which claims the benefit of U.S. Provisional Application No. 61/716,788, filed Oct. 22, 2012, and the benefit of Netherlands Application No. NL 2009674, filed Oct. 22, 2012, the contents of all of which are incorporated by reference herein.

FIELD OF THE INVENTION

The present invention relates to a process for the preparation of benzene derivatives, more in particular, to a process for the preparation of benzene derivatives obtained via a reaction of a furan derivative with ethylene.

BACKGROUND OF THE INVENTION

In recent times a tendency has grown to obtain a variety of chemicals from renewable resources. In this context there has been a tendency to create chemicals from biomass carbohydrates, such as cellulose, starch, hemicellulose, sugars and the like. Under dehydration conditions these carbohydrates can be converted into a number of interesting chemicals, including levulinic acid and derivatives and hydroxymethylfurfural and derivatives. It would be of interest to use these chemicals for the production of added value chemical compounds.

One such added value chemical compound is constituted by terephthalic acid. Terephthalic acid is widely used in the preparation of polyesters. To make these polyesters the terephthalic acid is usually reacted with a diol, such as ethylene glycol, trimethylene glycol butane diol, or higher glycols. The polyester thus obtained finds ample application in containers, bottles, films, fibres and other packaging materials. Terephthalic acid is commonly prepared by the oxidation of para-xylene. Para-xylene is generally obtained from a refinery process in the treatment of crude oil, e.g. from a reforming process. It is evident that crude oil is not a renewable resource. Therefore, it would be desirable to provide a process wherein terephthalic acid would become available from a renewable source, such as biomass carbohydrates. Also para-xylene production from crude oil is tight and may hamper future PET growth, specifically in Asia.

In U.S. Pat. No. 7,385,081 a process has been disclosed wherein biomass is being dehydrated to yield 5-hydroxymethylfurfural, which can be oxidized to yield 2,5-furandicarboxylic acid. The dicarboxylic acid obtained is subsequently subjected to a Diels Alder reaction with ethylene to yield a bicyclic ether which is then dehydrated to produce terephthalic acid. The process described in U.S. Pat. No. 7,385,081 indeed used renewable starting material. The process also showed that terephthalic acid can be obtained via this process. The conditions that can be applied to the Diels Alder reactions include an ethylene pressure in the range of from 10 psig to about 2000 psig (about 1.7 to 139 bar abs), with a preferred pressure of 100 to 300 psig (about 7.9 to 21.7 bar abs). Reaction temperatures may be varied between 100 and 250° C. The reaction may be conducted in the presence of a solvent, such as water, DMSO, N-methyl-2-pyrrolidone, N,N-dimethylformamide, $C_1$-$C_{10}$ alcohols, $C_2$-$C_6$ ketones and $C_2$ to $C_{10}$ esters. However, the examples in this patent specification wherein ethylene pressures ranging from 100 to 250 psig (7.9 to 18.2 bar abs) and temperatures of 100 to 200° C. were applied and water or methanol was present as solvent, show that the yield of terephthalic acid is very low. The highest estimated yield was 0.14 mole % based on the amount of 2,5-furandicarboxylic acid charged. Such low yields of the product following the Diels Alder reaction would render this process unsatisfactory and commercially unattractive.

Another route to arrive at terephthalic acid has been described in WO 2010/151346. According to the process described herein a hexose is converted to 5-hydroxymethylfurfural, which is hydrogenated to 2,5-dimethylfuran. This product is reacted with ethylene under cycloaddition reaction conditions and in the presence of a solid catalyst to produce p-xylene. The p-xylene, thus produced, may be oxidized to produce terephthalic acid. The cycloaddition reaction conditions typically include a temperature range of 100 to 300° C. and an ethylene partial pressure of about 10 to about 100 bar. The use of solvents, such as DMSO, is advantageously reduced or even eliminated so that solvent-free or substantially solvent-free reaction mixtures are employed. Amongst the solid catalysts mentioned reference is made to activated carbon, silica gel, alumina, zirconia and molecular sieves. These catalysts are present in small amounts such as 2% wt, based on 2,5-dimethylfuran. In the process byproducts are produced, such as 2,5-hexanedione. Although yields of the desired benzene derivative are higher than in the process of U.S. Pat. No. 7,385,081 the contamination with significant amounts of byproduct makes this process also unattractive.

SUMMARY OF THE INVENTION

Therefore, there is still a desire to provide a process that enables the preparation of terephthalic acid and that starts from a renewable source, wherein the yield and/or selectivity of the desired product is improved compared to the prior art processes according to U.S. Pat. No. 7,385,081 and WO 2010/151346.

DETAILED DESCRIPTION OF THE INVENTION

It has now been found that higher product yields can be obtained and the forming of byproducts can be reduced or eliminated if the reaction between a furan derivative and ethylene is carried out in the presence of an acid solvent. Accordingly, the present invention provides a process for the preparation of benzene derivatives of the formula (I);

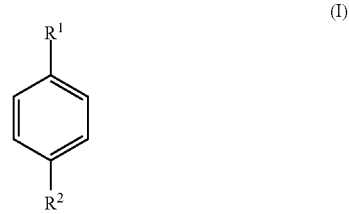

wherein $R^1$ and $R^2$, are the same or different and independently are selected from the group consisting of hydrogen, alkyl, aralkyl, —CHO, —$CH_2OR^3$, —$CH(OR^4)(OR^5)$ and —$COOR^6$, wherein $R^3$, $R^4$ and $R^5$ are the same or different and are selected from hydrogen, alkyl, aryl, alkaryl, aralkyl, alkylcarbonyl or arylcarbonyl, or wherein $R^4$ and $R^5$ together form an alkylene group and wherein $R^6$ is selected from hydrogen, alkyl and aryl,
which process comprises:
reacting a furan derivative of formula (II):

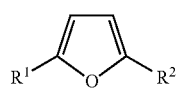
(II)

wherein $R^1$ and $R^2$ have the meanings above,
with ethylene under cycloaddition reaction conditions in the presence of an acid solvent to produce the benzene derivative, wherein the acid solvent is a carboxylic acid and is present in a weight ratio acid solvent to furan derivative from 1:1 to 250:1.

Without wishing to be bound to any theory it is believed that the benzene derivative is prepared by a first Diels Alder reaction between the furan derivative of formula (II) with ethylene to form a bicyclic ether, and by a subsequent in situ reaction of this bicyclic ether wherein water is split off and aromatization occurs to yield the benzene derivative. The acid solvent appears to act as dehydrating agent.

The furan derivative that is being used as starting material may be unsubstituted or contain substituents that have independently been selected from the group consisting of alkyl, aralkyl, —CHO, —$CH_2OR^3$, —$CH(OR^4)(OR^5)$ and —$COOR^6$, wherein $R^3$, $R^4$ and $R^5$ are the same or different and are selected from hydrogen, alkyl, aryl, alkaryl, aralkyl, alkylcarbonyl or arylcarbonyl, or wherein $R^4$ and $R^5$ together form an alkylene group and wherein $R^6$ is selected from hydrogen, alkyl and aryl. If $R^4$ and $R^5$ together form an alkylene group a ring structure is being formed. Preferably, the ring structure is a five- or six-membered ring. Therefore, in such a case $R^4$ and $R^5$, preferably, form together an ethylene or a trimethylene group. Suitably, $R^1$ and $R^2$ independently comprise 1 to 8 carbon atoms, optionally in addition to one or more oxygen atoms. When $R^1$ and/or $R^2$ are/is alkyl, the alkyl group suitably comprises from 1 to 6 carbon atoms, more preferably being methyl or ethyl. Preferably at least one of $R^1$ and $R^2$ is alkyl, the alkyl group suitably comprising from 1 to 6 carbon atoms, more preferably being methyl or ethyl. When $R^1$ and/or $R^2$ are/is aryl, the aryl group, which is optionally substituted, comprises suitably from 6 to 10 carbon atoms, more preferably being phenyl. It is observed that when $R^1$ and/or $R^2$ are/is alkyl, aryl, alkaryl or aralkyl, $R^1$ and $R^2$ may contain one or more heteroatoms-containing substituents, such as a halogen atom, cyano group, and nitrogen or sulphur-containing groups such as amino, alkylated amino, nitro and mercaptyl groups. When $R^1$ and/or $R^2$ contain/s more than one carbon atom they may also comprise an additional hydroxy or alkoxy groups as substituent. Also $R^3$, $R^4$, $R^5$ and $R^6$ may contain one or more substituents selected from halogen atoms, cyano, nitro, amino, alkylated amino, mercaptyl, hydroxyl and alkoxy groups. $R^3$, $R^4$, $R^5$ and $R^6$ may suitably comprise from 1 to 7, with more preference from 1 to 4 carbon atoms.

It is advantageous if the furan derivative that is being used as starting material can be directly derived from a biomass resource. Recently there has been work done on the conversion of carbohydrates to ethers and esters of 5-hydroxymethyl furfural. An example of such work is described in WO 2007/104514 as to the ethers and in WO 2007/104515 as to the esters of 5-hydroxymethyl furfural. In these patent applications the conversion of a carbohydrate to the ether or ester, respectively, has been described wherein the carbohydrate is converted into the desired product in one step. Since it is advantageous to have the furan derivative of the present invention been made available via the most convenient method, the furan derivative of the present invention has preferably been derived form the dehydration of a carbohydrate. As disclosed in the above-mentioned patent applications, the carbohydrate is suitably selected from polysaccharides, oligosaccharides, disaccharides and monosaccharides. The components of particular interest in biomass are those feedstocks that contain a monosaccharide. Examples of suitable monosaccharides include fructose and mixtures of fructose with other monosaccharides, such as other hexoses and/or pentoses. A hexose is a monosaccharide with six carbon atoms having the chemical formula $C_6H_{12}O_6$. Hexoses may be classified by functional group, with aldohexoses having an aldehyde at position 1, and ketohexoses having a ketone at position 2. Fructose is a ketohexose. Suitable other hexoses include but are not limited to glucose, galactose, mannose, and their oxidized derivatives, e.g. aldonic acid, reduced derivatives, e.g. alditol, etherified, esterified and amidated derivatives. A pentose is a monosaccharide with five carbon atoms, having the chemical formula $C_5H_{10}O_5$. They may either have an aldehyde functional group in position 1 (aldopentoses), or a ketone functional group in position 2 (ketopentoses). Suitable 5-carbon monosaccharides include but are not limited to arabinose, ribose, ribulose, xylose, xylulose and lyxose.

The di- and oligosaccharide carbohydrates containing more than one saccharide unit, are suitably hydrolysed, resulting in a mixture of dissolved di- and/or oligosaccharides, monomeric saccharide units and/or glycoside units. Examples of suitable disaccharides include maltose, lactose, trehalose, turanose and sucrose, sucrose being preferred. Sucrose is abundantly available and therefore very suitable. The disaccharides can easily be converted into the monomeric units. Examples of suitable oligosaccharide are fructo-oligosaccharides which are found in many vegetables. By oligosaccharides is understood a carbohydrate that is built up of 3 to 10 monosaccharide units. Polysaccharides have more than ten monosaccharide units. These are polymeric structures formed of repeating units joined together by glycosidic bonds. The number of monosaccharide units in a polysaccharide may vary widely, and may range from 10 to 3000. Suitable polysaccharides include fructan, i.e. a polymer of fructose moieties, and levan, which is composed of D-fructofuranosyl moieties. Mixtures may also be used. Starch, hemi-cellulose and in particular cellulose can also be used as starting material, especially if they stem from hydrolysis process streams from enzymatic or catalytic hydrolysis of starch, cellulose and hemi-cellulose or from alcoholysis processes that already contain mono- and disaccharides. In view of the above, the preferred monosaccharide is fructose, glucose and mixtures thereof. The preferred disaccharide is sucrose.

As the conversion of a carbohydrate with an alcohol is preferred and since the conversion of the carbohydrate with lower alcohols and water run smoothly, the furan derivative of the present invention preferably has substituents that can easily be obtained by such conversions. Therefore, a furan is preferably used wherein $R^1$ and $R^2$ which are the same or different, are selected from —CHO, —$CH_2OR^3$ and —$CH(OR^4)(OR^5)$ wherein $R^3$, $R^4$ and $R^5$ are the same or different and are hydrogen or a $C_1$-$C_6$ alkyl group. More preferably, $R^1$ is CHO and $R^2$ is —$CH_2OR^3$, wherein $R^3$ is hydrogen, methyl or ethyl.

It is also possible to subject the products that have been obtained after the conversion of the carbohydrate to a further treatment. It may be advantageous to subject such products to a further oxidation to convert one or both of $R^1$ and $R^2$ to substituents that contain a carboxylate group. When both $R^1$ and $R^2$ are carboxylate group-containing substituents, i.e. being —$COOR^6$, and when such compounds are subjected to the process of the present invention the product obtained will then directly comprise terephthalate moieties. It is therefore advantageous that at least one of $R^1$ and $R^2$ is a —$COOR^6$ group, preferably both $R^1$ and $R^2$ are —$COOR^6$ groups.

On the other hand, it would also be possible to subject the products of the conversion of the carbohydrate to a reduction such that the substituents $R^1$ and/or $R^2$ are converted into alkyl groups, in particular to methyl, ethyl or isopropyl groups. The advantage thereof resides in that the process of the present invention will run more smoothly when the furan derivative of formula (II) contains alkyl groups as substituents, compared to the less electron-withdrawing substituents like —CHO, —$CH_2OR^3$, —$CH(OR^4)(OR^5)$ and $COOR^6$. In order to obtain terephthalic acid an additional oxidation would be required. Such oxidation can be accomplished in existing facilities which makes this option an interesting proposition.

According to the present invention the reaction of the furan derivative and ethylene is carried out in the presence of an acid solvent. The acid solvent is a carboxylic acid. The carboxylic acid may suitably contain 1 to 16 carbon atoms, advantageously from 1 to 8 carbon atoms. The acid solvent may be aliphatic, cycloaliphatic or aromatic. Suitable examples include formic acid, acetic acid, propionic acid, butyric acid, valeric acid, but also benzoic acid or a toluic acid or mixtures of one or more of the above.

The process according to the present invention is suitably carried out under cycloaddition conditions in the presence of the acid solvent as a dehydrating agent and preferably in the presence of a desiccating agent, which is a water removing agent. By desiccating agent is understood a chemical substance that has such a great affinity for water that it will abstract water from a great many fluid materials. The substance may be soluble or insoluble under the reaction conditions. It has been found that the presence of a desiccating agent reduces the formation of byproducts, such as diketone derivatives, especially when the reaction is conducted at relatively low temperatures, i.e. at temperatures in the range of 100 to 250° C. In particular, the presence of a desiccating agent is desirable when the reaction of 2,5-dimethylfuran is conducted at such relatively low temperatures to reduce the formation of 2,5-hexadione. Desiccating agents are also sometimes referred to as desiccants or dehydration agents. The desiccating agent is suitably present in an amount sufficient to absorb the water formed during the water elimination of the cycloaddition intermediate.

The desiccating agent must be present in amounts larger than a catalytic amount. The person skilled in the art will realize that the amount of desiccating agent is suitably selected such that it is at least present in an amount to absorb all water that is released in the cycloaddition intermediate dehydration reaction. Since one mole of furan derivative releases one mole of water, the amount of desiccating agent is suitably at least present in a stoichiometric amount if the desiccating agent is capable of absorbing one molecule of water per molecule. For other desiccating agents that absorb less well-defined amounts of water, such as silica gel, clays or molecular sieves the amount can be determined based on the expertise of the skilled person. Preferably, the desiccating agent is present in excess. Typically, the amount of desiccating agent is in the range of from 50 to 1000% wt, based on the amount of the furan derivative.

The desiccating agent can be selected from a wide range of known desiccants. Examples of inorganic desiccants include silica gel, activated charcoal, anhydrous calcium sulphate, anhydrous calcium chloride, montmorillonite clay and molecular sieves. It will be appreciated that some of these compounds have been mentioned as catalysts in the cycloaddition reaction of WO 2010/151346. However, in the reaction of WO 2010/151346 the catalysts were present in a small amount and not in an amount sufficient to absorb water that emerged from the cycloaddition reaction.

In addition to inorganic desiccating agents, there is a range of organic desiccating agents which are preferably used in the process according to the invention. The organic desiccating agent may e.g. be a cation modified polyacryl amide, cationic polyacrylic ester and the like. Preferably, the organic desiccating agent is a carboxylic acid anhydride. The anhydride may react with any water that is present and/or emerges in the mixture containing the ethylene and furan derivative to yield the carboxylic acid. In this way, water molecules are withdrawn from the reaction mixture so that they cannot lead to by-products. It is surprising that these organic desiccating agents perform much better than silica gel and molecular sieves which are known to be inorganic desiccating agents.

The organic carboxylic acid anhydride may be selected from a wide range of carboxylic acids. Both mono-carboxylic acids and poly-carboxylic acids can be used. The number of carbon atoms in the carboxylic acid anhydrides may range from 1 to 18 carbon atoms, suitably from 2 to 8 carbon atoms. The carboxylic acids may be aliphatic or aromatic. Examples of suitable mono-carboxylic anhydrides include formic anhydride, acetic anhydride, propionic anhydride, butanoic anhydride, valeric anhydride, hexanoic anhydride and benzoic anhydride. Suitable examples of poly-carboxylic acid anhydrides include malic anhydride, succinic anhydride and malonic anhydride. Acetic anhydride and benzoic anhydride and mixtures thereof are particularly preferred. If the desiccating agent is a liquid under the reaction conditions, it will be part of the solvent system.

The process according to the present invention can be conducted in the presence of an additional dehydration catalyst in addition to the acid solvent. Such catalysts include those that have been described in WO 2010/151346. As indicated above, it is believed that the reaction takes place in two stages; a first stage wherein a Diels Alder reaction takes place and wherein the furan derivative and ethylene react to form a bicyclic ether and a subsequent stage wherein the bicyclic ether releases water in a dehydration reaction and aromatization takes place to yield a benzene derivative. Therefore, it is possible to employ a Diels Alder catalyst as additional dehydration catalyst. Known Diels Alder catalysts include Lewis acids, e.g. aluminium, boron, zinc, hafnium or iron compounds, such as $AlCl_3$, $Al(Et)Cl_2$, $Al(Et)_2Cl$, $BF_3$, $B(Ac)_3$, $ZnCl_2$, $ZnBr_2$, $Zn(Ac)_2$, $FeCl_3$, $Fe(Ac)_3$, $FeCl_2$ and $Fe(Ac)_2$, Brønsted acids, such a inorganic mineral acids, e.g. sulphuric acid, phosphoric acid, nitric acid, hydrobromic acid or hydrochloric acid, and organic acids, such as methane sulphonic acid, p-toluenesulphonic acid, or carboxylic acids. Diels Alder catalysts also include halides of tin or titanium, such as $SnCl_4$ and $TiCl_4$. Alternatively, activated carbon, silica, alumina, silica-alumina, zirconia or zeolites may be used. Carbon, silica, alumina, silica-alumina, zirconia and zeolites may be used as such, but they may also be used as support for a catalytically active metal or metal compound. Such metals or metal compounds suitably include alkali metals, alkaline earth metals, transition metals, noble metals, rare earth metals. Preferably, the catalysts are acidic, e.g. by treating supports with phosphoric acid, or by ion exchange of zeolites to render them into their acidic form. More preferably, the catalyst is an acid catalyst. Examples of solid catalysts include amorphous silica-alumina, zeolites, preferably zeolites in their H-form, and acidic ion exchange resins. Other suitable catalysts that are liquids or that may be dissolved in the appropriate solvent to yield a homogeneous catalyst environment, include organic and inorganic acids, such as alkane carboxylic acid, arene carboxylic acid, sulphuric acid, phosphoric acid, hydrochloric acid, hydrobromic acid and nitric acid.

Surprisingly, it has been found that excellent results are obtained when just a carboxylic acid solvent is used as a dehydrating agent. It was found that the process of the present invention is conducted very smoothly when the carboxylic acid solvent and the desiccating agent have been derived from the same carboxylic acid. Thus, preferably the desiccating agent is a carboxylic acid anhydride and the acid solvent is a carboxylic acid derived from this carboxylic acid anhydride. Also in that case, the carboxylic anhydride is after reaction with water converted into the acid solvent (e.g. acetic anhydride+$H_2O$→2 acetic acid).

The amount of the additional dehydration catalyst may vary between wide ranges. Typically, such catalysts are employed in relatively small amounts, such as those disclosed in WO 2010/151346. Suitably, the amount of additional dehydration catalyst is at least 0.5% wt, based on the furan derivative. Preferably, the amount is in the range of from 0.5 to 5% wt, based on the furan derivative. When the acid solvent is a carboxylic acid that acts as dehydrating agent, the amount thereof may be up to 1000% wt, based on the furan derivative. Also higher amounts are possible, as may be determined by the skilled person, e.g. dependent on the desired amount of acid solvent.

It is feasible to use a mixture of the carboxylic acid anhydride desiccating agent and a carboxylic acid as solvent system for the furan derivative and ethylene. It may appear advantageous to include an additional solvent in the mixture of furan derivative, ethylene, acid solvent and optionally desiccating agent. Such additional solvents may be selected from a range of compounds. The use of a solvent is convenient if the furan derivative is solid under the reaction conditions. The liquid phase thus obtained makes it easier to handle the reactants and the reaction products. Thereto, the solvent may be selected from a wide range of potential liquids. Suitably, the additional solvent is selected from the group consisting of water, esters, ketones, amides, aldehydes, acids, ethers, aliphatic or aromatic hydrocarbons, ionic liquids and sulphoxides. It is evident that when the additional solvent is an acid, it is different from the acid solvent. Advantageously, the additional solvents are organic and contain from 1 to 20 carbon atoms. Suitable esters include the $C_1$-$C_{10}$ alkyl esters of $C_1$-$C_6$ carboxylic acids, such as methyl formate, methyl acetate, ethyl formate, ethyl acetate, methyl propionate, ethyl propionate, methyl butyrate, ethyl butyrate and ethylhexyl acetate. Suitable ketones contain 2 to 8 carbon atoms, such as acetone, butanone and methyl iso-butyl ketone. Suitable amides include acetamide and formamide, optionally substituted by one or two alkyl groups with 1 to 6 carbon atoms. Examples of suitable ethers include di($C_1$-$C_6$ alkyl) ethers, such as dimethyl ether, diethyl ether and methyl tert-butyl ether, and also cyclic ethers such as tetrahydrofuran. Suitable aldehydes include $C_1$-$C_6$ aldehydes, such as formaldehyde, acetaldehyde, propanal and hexanal. A suitable sulphoxide is dimethylsulphoxide. Although it is possible to use hydrocarbon solvents such as alkanes, e.g. pentane, hexane, cyclohexane, heptane, or aromatics, such as benzene or toluene, it is preferred to use polar solvents. The reaction is particularly facilitated when the additional solvent also dissolves ethylene to some extent. Therefore, the additional solvent is advantageously selected from ketones, such as acetone.

According to the invention the reaction is conducted in the presence of an acid solvent comprising a carboxylic acid. When a carboxylic acid anhydride-containing desiccating agent is used in the process of the present invention the acid solvent suitably comprises a carboxylic acid from which such a carboxylic acid anhydride has been formed. Advantageously, the amounts of carboxylic acid anhydride-containing desiccating agent and carboxylic acid-containing solvent are selected such that no other solvents are required. The amount of acid solvent may be determined by the skilled person. In case of solid furan derivatives the amount should suitably be such that the reaction mixture becomes liquid. The weight ratio acid solvent to furan derivative is typically from 1:1 to 250:1. If a carboxylic acid anhydride is used as desiccating agent and a carboxylic acid is used as acid solvent, the weight ratio carboxylic acid anhydride to carboxylic acid is suitably from 1:99 to 5:1, preferably from 5:95 to 2:1. Good results have been achieved at weight ratios ranging from 10:90 to 1:1. As one water molecule is liberated per molecule of furan derivative, the molar ratio of a carboxylic acid anhydride to furan derivative of formula II is suitably from 10:1 to 1:1, preferably from 3:1 to 1:1.

The reaction of the furan derivative and ethylene may suitably be carried out under conditions that are similar to those of the formation of a bicyclic ether from 2,5-furan dicarboxylic acid and ethylene, as described in U.S. Pat. No. 7,385,081 and the cycloaddition conditions that have been disclosed in WO 2010/151346. Such suitable conditions include a temperature in the range from 100 to 450° C. A preferred temperature range is from 150 to 400° C., more preferably from 180 to 350° C. At the preferred low temperatures, i.e. from 100 to 250° C., the presence of a desiccating agent is desirable. It has been found that relatively high temperatures, i.e. temperatures from 250 to 450° C., are advantageous since at these temperatures the reaction does not yield many by-products. Especially the production of diketones is reduced. It is believed that at these high temperatures any diketone formed may react back to the furan derivative from which it originates via ring closure. Ethylene is typically provided via applying an elevated ethylene partial pressure. The ethylene partial pressure is suitably at least 10 bar. It is believed that this allows an improved contact between ethylene and the furan derivative. These pressures also provide a sufficient amount of ethylene to ensure an efficient reaction. Higher pressures also enhance the reaction rate. It is also feasible to conduct the reaction in a supercritical ethylene phase. In such cases the pressure may be raised above about 50 bar. The use of a supercritical compound in a solvent results in a gas expanded liquid. Preferably the reaction pressure is such that at the selected reaction temperature most of the ethylene that is present in the reactor is present in the supercritical form. Typically, this means a reaction temperature of e.g. 180 to 320° C., and a pressure of e.g. 50-1000 bar. Since the use of very high pressures does not seem to incur any further benefits, the ethylene pressure at the reaction conditions is suitably from 30 to 100 bar.

The furan derivative of formula (II) is suitably reacted with ethylene for 0.5 to 72 hours, preferably from 3 to 48 hours It is observed that at higher pressures the reaction rate increases and the reaction time may be shortened, e.g. to a range of 0.5 to 24 hours. In the reaction, ethylene may be added in a batchwise, a semi-continuous or a continuous fashion. In a batchwise fashion both the furan derivative and ethylene are charged to a vessel, e.g. an autoclave, and made to react with each other. In a semi-continuous fashion, the furan derivative is charged to a vessel and a stream of ethylene is continuously contacted with the furan derivative, e.g. by supplying pressurised ethylene gas through a furan derivative-containing liquid phase. In a continuous fashion both a stream of furan derivative and a stream of ethylene are fed to a reactor where they are contacted and from which reactor continuously a stream of product is withdrawn. It is especially advantageous in the case of a semi-continuous or continuous process to separate unconverted furan derivative and/or ethylene from the reaction product and recycle these starting materials. Such a procedure provides the skilled person with a degree of freedom to select the most appropriate residence time in the employed reactor. In a continuous process the liquid hourly space velocity (LHSV) may suitably be from 0.01 to 10 $hr^{-1}$, preferably from 0.05 to 5 $hr^{-1}$.

As indicated above, the process according to the present invention is very suitable for providing an intermediate in the production of terephthalic acid. Accordingly, the present invention further provides the use of the products of the process according to the invention in the preparation of terephthalic acid. This is especially advantageous when $R^1$ and $R^2$ in the furan derivative of formula (II) are selected from alkyl, —CHO, —$CH_2OR^3$ and —$CH(OR^4)(OR^5)$, wherein $R^3$, $R^4$ and $R^5$ have the meaning as described above. Terephthalic acid may then conveniently be prepared by oxidizing the para-substituted benzene derivative prepared according to the process of the present invention. Accordingly, the present invention provides a process for the preparation of terephthalic acid by recovering a para-substituted benzene derivative of the formula (I);

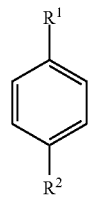

(I)

wherein $R^1$ and $R^2$, are the same or different and independently are selected from the group consisting of alkyl, —CHO, —$CH_2OR^3$ and —$CH(OR^4)(OR^5)$, wherein $R^3$, $R^4$ and $R^5$ are the same or different and are selected from hydrogen, alkyl, aryl, alkylcarbonyl or arylcarbonyl, or wherein $R^4$ and $R^5$ together form an alkylene group, which has been prepared according to the process described above, and oxidizing the thus obtained para-substituted benzene derivative to yield terephthalic acid. The oxidation of the benzene derivative obtained may be effected in any conventional oxidation method, as will be appreciated by the skilled person. A suitable oxidation is effected by using an oxygen-containing gas in the presence of a catalyst that comprises cobalt and manganese. Aromatic carboxylic acids may suitably be prepared over a catalyst that contains bromine in addition to cobalt and manganese. Preparation of such catalysts has e.g. been described U.S. Pat. No. 4,138,354. The oxygen-containing gas may be air, oxygen-enriched air or substantially pure oxygen.

The temperature and pressure in of the oxidation can be selected from wide ranges. The pressure of the reaction mixture is preferably between 5 and 100 bar, with a preference for pressures between 10 and 80 bar. In case the oxidant is an oxygen-containing gas, such as air, the gas can be continuously fed to and removed from the reactor, or the gas can be supplied all at the start of the reaction. In the latter case, the pressure of the system will depend on the headspace volume and the amount of gas required to convert the starting material. It is clear that in the latter case, the pressure of the system may be significantly higher than when an oxygen containing gas is continuously fed and removed.

The temperature of the reaction mixture is suitably between 60 and 220° C., preferably between 100 and 210° C., more preferably between 150 and 200° C., most preferably between 160 and 190° C.

In the preferred oxidation catalysts, molar ratios of cobalt to manganese (Co/Mn) are typically 1/1000-100/1, preferably 1/100-10/1 and more preferably 1/10-4/1.

Likewise, in the preferred oxidation catalysts, molar ratios of bromine to metals (e.g. Br/(Co+Mn)) are typically from 0.001 to 5.00, preferably 0.01 to 2.00 and more preferably 0.1 to 0.9.

Catalyst concentration (calculated on the metal, e.g., Co+Mn) is preferably between 0.1 and 10 mol % relative to the starting material, with a preference for loads between 2 and 6 mol %. Good results were obtained in general with catalyst loads of around 4 mol %.

Reaction times suitably range from 0.1 to 48 hours, preferably, from 0.5 to 24 hrs.

The invention will be further illustrated by means of the following examples.

Example 1

In experiments 1 to 4 1.5 mL of 2,5-dimethylfuran (1.3 g) was contacted with ethylene at a temperature of 150° C. at an ethylene pressure of 40 bar in the presence of a dehydration catalyst. (In experiment 1 no catalyst and no solvent was present.) The catalysts were selected from silica gel having a surface area of 519 $m^2$/g and a pore volume of 0.9 mL/g ("Cat 1"), 1% wt Pd on activated carbon ("Cat 2"), and 5% wt Pd and 1% wt Fe on activated carbon ("Cat 3"). In the experiments 5 to 19 150 mg 2,5-dimethylfuran was dissolved in acetic acid, acetic anhydride or both, as indicated in Table 1. The reaction mixtures according to the invention included an acid solvent, the solvent being acetic acid ("AcOH"), which also has a function as dehydrating agent. In other experiments according to the invention acetic acid anhydride ("AcOAc") was added as desiccating agent and/or any of the above-mentions catalysts as additional dehydration catalyst. The yields on p-xylene ("pXy") and the by-product 2,5-hexanedione ("HDO") were determined after 20 hours. The yields were expressed as mole percent, based on the number of moles of the 2,5-dimethylfuran starting material. The results are shown in Table 1.

TABLE 1

| Exp. No. | Catalyst | Amount Catalyst, mg | Solvent | Amount, mL | pXy, % | HDO, % |
|---|---|---|---|---|---|---|
| 1 | — | — | — | — | 0.0 | 0.0 |
| 2 | 1 | 200 | — | — | 4.7 | 0.4 |
| 3 | 2 | 80 | — | — | 9.2 | 7.1 |
| 4 | 3 | 80 | — | — | 6.9 | 16.7 |
| 5 | — | — | AcOH | 1.0 | 8.8 | 0.5 |
| 6 | 1 | 80 | AcOH | 1.0 | 9.0 | 1.6 |
| 7 | 2 | 80 | AcOH | 1.0 | 8.8 | 2.7 |
| 8 | — | — | AcOH / AcOAc | 0.9 / 0.1 | 7.8 | 0.0 |
| 9 | 1 | 80 | AcOH / AcOAc | 0.9 / 0.1 | 9.2 | 0.0 |
| 10 | 2 | 80 | AcOH / AcOAc | 0.9 / 0.1 | 8.7 | 0.0 |
| 11 | — | — | AcOH / AcOAc | 0.5 / 0.5 | 7.9 | 0.0 |
| 12 | 1 | 80 | AcOH / AcOAc | 0.5 / 0.5 | 9.3 | 0.0 |
| 13 | 2 | 80 | AcOH / AcOAc | 0.5 / 0.5 | 9.5 | 0.0 |
| 14 | — | — | AcOH / AcOAc | 0.05 / 0.95 | 5.1 | 0.0 |
| 15 | 2 | 80 | AcOH / AcOAc | 0.05 / 0.95 | 3.2 | 0.0 |
| 16 | — | — | AcOAc | 1.0 | 0.7 | 0.0 |
| 17 | 1 | 80 | AcOAc | 1.0 | 0.6 | 0.0 |
| 18 | 2 | 80 | AcOAc | 1.0 | 2.1 | 0.0 |
| 19 | 3 | 80 | AcOAc | 1.0 | 7.5 | 0.0 |

From the above results it is apparent that the presence of acetic acid as acid solvent results in an improved yield of the desired benzene derivative and/or a reduction of the formation of diketone by-product. The results further show that the use of acetic acid anhydride as desiccating agent suppresses the forming of the hexanedione by-product considerably.

Example 2

To show the influence of the reaction temperature on the yields a series of experiments was run, similar to the experiments 5 to 19 in Example 1, but at a temperature of 200° C. for 4 hours. The results thereof are shown in Table 2.

TABLE 2

| Exp. No. | Catalyst | Amount Catalyst, mg | Solvent | Amount, mL | pXy, % | HDO, % |
|---|---|---|---|---|---|---|
| 20 | — | — | AcOH / AcOAc | 0.9 / 0.1 | 22.3 | 0.0 |
| 21 | 1 | 80 | AcOH / AcOAc | 0.9 / 0.1 | 26.1 | 0.0 |
| 22 | 2 | 80 | AcOH / AcOAc | 0.9 / 0.1 | 25.2 | 0.0 |
| 23 | — | — | AcOH / AcOAc | 0.5 / 0.5 | 15.9 | 0.0 |
| 24 | 1 | 80 | AcOH / AcOAc | 0.5 / 0.5 | 20.2 | 0.0 |
| 25 | 2 | 80 | AcOH / AcOAc | 0.5 / 0.5 | 20.8 | 0.0 |

The results show that the yield can be increased considerably by applying higher temperatures than those applied in the experiments of Example 1.

Example 3

Experiments were run in a manner similar to that of experiments 5 to 19 in Example 1 at a reaction temperature of 150° C. for 20 hours in the absence of any additional catalyst. Different ethylene pressures were applied. Moreover, the solvent has been varied; in addition to acetic acid, propionic acid ("PrOH") or benzoic acid ("BzOH") was used. The yields of pXy and HDO are shown in Table 3.

TABLE 3

| Exp. No. | Ethylene pressure, bar | Solvent | Amount, mL | pXy, % | HDO, % |
|---|---|---|---|---|---|
| 26 | 50 | AcOH / AcOAc | 0.75 mL / 0.25 mL | 10.0 | 0.0 |
| 27 | 30 | AcOH / AcOAc | 0.75 mL / 0.25 mL | 6.4 | 0.0 |
| 28 | 50 | PrOH / AcOAc | 0.75 mL / 0.25 mL | 6.3 | 0.0 |
| 29 | 30 | PrOH / AcOAc | 0.75 mL / 0.25 mL | 5.6 | 0.0 |
| 30 | 50 | BzOH / AcOAc | 0.75 g / 0.25 mL | 12.1 | 0.0 |
| 31 | 30 | BzOH / AcOAc | 0.75 g / 0.25 mL | 7.8 | 0.0 |

The above results show that different carboxylic acids may be used as solvent and dehydration catalyst. Pressure differences seem to play a minor role.

Example 4

In another series of experiments similar to those of experiments 5 to 19 in Example 1, ethylene was pressurised at room temperature to 30 bar. The reaction temperature was varied between 200, 220 and 240° C. The reaction time was 4 hr. The solvent/dehydration catalyst was selected from acetic acid, propionic acid, benzoic acid, valeric acid ("ValOH") and succinic acid ("SucOH"). The yields of p-xylene and 2,5-hexanedione were determined as in the previous experiments. The results are shown in Table 4.

TABLE 4

| Exp. No. | Temperature, ° C. | Solvent | Amount, mL | pXy, % | HDO, % |
|---|---|---|---|---|---|
| 32 | 200 | AcOH / AcOAc | 0.75 / 0.25 | 26.7 | 0... |
| 33 | 220 | AcOH / AcOAc | 0.75 / 0.25 | 37.6 | 0.0 |
| 34 | 240 | AcOH / AcOAc | 0.75 / 0.25 | 39.6 | 0.0 |
| 35 | 200 | PrOH / AcOAc | 0.75 / 0.25 | 14.0 | 0.0 |
| 36 | 220 | PrOH / AcOAc | 0.75 / 0.25 | 16.2 | 0.0 |
| 37 | 240 | PrOH / AcOAc | 0.75 / 0.25 | 19.2 | 0.0 |
| 38 | 200 | ValOH / AcOAc | 0.75 g / 0.25 mL | 5.3 | 0.0 |
| 39 | 220 | ValOH / AcOAc | 0.75 g / 0.25 mL | 6.2 | 0.0 |
| 40 | 240 | ValOH / AcOAc | 0.75 g / 0.25 mL | 8.2 | 0.0 |
| 41 | 200 | BzOH / AcOAc | 0.75 g / 0.25 mL | 16.0 | 0.0 |
| 42 | 220 | BzOH / AcOAc | 0.75 g / 0.25 mL | 27.9 | 0.0 |
| 43 | 240 | BzOH / AcOAc | 0.75 g / 0.25 mL | 33.8 | 0.0 |
| 44 | 200 | SucOH / AcOAc | 0.75 g / 0.25 mL | 9.3 | 3.5 |
| 45 | 220 | SucOH / AcOAc | 0.75 g / 0.25 mL | 20.5 | 0.0 |
| 46 | 240 | SucOH / AcOAc | 0.75 g / 0.25 mL | 33.7 | 0.0 |

The results further confirm that at increasing temperatures the yield increases also.

Example 5

To show that different carboxylic acid anhydrides can be used experiments were conducted in a way similar to that in Example 3. The reaction temperature was 210° C., the ethylene pressure was set at 30 bar and the reaction had a duration of 24 hours. The carboxylic acid anhydride used in these experiments were selected from AcOAc, benzoic acid anhydride ("BzOBz") and propionic acid anhydride ("PrOPr"). The resulting yields on pXy and HDO are shown in Table 5.

TABLE 5

| Exp. No. | Solvent | Anhydride | Amount | pXy, % | HDO, % |
| --- | --- | --- | --- | --- | --- |
| 47 | AcOH, 0.75 mL | AcOAc | 0.25 mL | 69.5 | 0.0 |
| 48 | AcOH, 0.75 mL | PrOPr | 0.25 mL | 77.9 | 0.0 |
| 49 | AcOH, 0.75 mL | BzOBz | 0.50 g | 76.6 | 0.0 |
| 50 | AcOH, 0.75 mL | BzOBz | 0.40 g | 84.7 | 0.0 |

These results show that the use of other carboxylic acid anhydrides also leads to advantageous yield of p-xylene. Benzoic acid anhydride proves to be very effective.

Example 6

To show that different substrates may be used in the process of the present invention 150 mg of different substrates were subjected to a reaction with ethylene. The substrates included 2-methylfuran ("2-MF"), 2,5-furan dicarboxylic acid ("FDCA") and the dimethyl ester of FDCA ("DM-FDCA"). The reaction with 2-MF was conducted in a solvent comprising acetic acid and either acetic acid anhydride or benzoic acid anhydride as desiccating agent. Temperature was set at 200 or 240° C. Ethylene pressure at room temperature was 30 bar. The yield of toluene ("Tol") was measured after 8 hr. The results of the experiments with 2-MF are shown in Table 6.

TABLE 6

| Exp. No. | Solvent | Anhydride | Amount | Temperature, ° C. | Tol, % |
| --- | --- | --- | --- | --- | --- |
| 51 | AcOH, 0.75 mL | AcOAc | 0.25 mL | 200 | 28.6 |
| 52 | AcOH, 0.75 mL | AcOAc | 0.25 mL | 240 | 35.6 |
| 53 | AcOH, 0.75 mL | BzOBz | 0.40 g | 200 | 37.2 |
| 54 | AcOH, 0.75 mL | BzOBz | 0.40 g | 240 | 57.5 |

FDCA and DM-FDCA were contacted with ethylene at 240° C. in a solvent/dehydration catalyst comprising acetic anhydride or phosphoric acid in amounts shown in the table below and one of acetic acid anhydride and benzoic acid anhydride. Ethylene pressure at room temperature was 30 bar. The benzene derivative that was formed was in all instances the acid, viz. terephthalic acid. That confirms the finding in U.S. Pat. No. 7,385,081 that also the diester of FDCA reacts to form terephthalic acid and that the dimethyl ester of terephthalic acid is not formed. The yield of terephthalic acid ("TPA") was measured after 32 hr. The results are shown in Table 7.

TABLE 7

| Exp. No. | Solvent | Anhydride | Amount | Substrate | TPA, % |
| --- | --- | --- | --- | --- | --- |
| 55 | AcOH, 0.75 mL | AcOAc | 0.25 mL | DM-FDCA | 7.2 |
| 56 | AcOH, 0.75 mL | AcOAc | 0.25 mL | FDCA | 6.8 |
| 57 | AcOH, 0.75 mL | BzOBz | 0.40 g | FDCA | 16.5 |
| 58 | AcOAc, 1.0 mL | H3PO4 | 5.0 µL | FDCA | 5.1 |
| 59 | AcOAc, 1.0 mL | H3PO4 | 5.0 µL | DM-FDCA | 11.6 |

These results show that terephthalic acid can be obtained in the process of the present invention in significantly higher yields than in the process according to U.S. Pat. No. 7,385,081.

Example 7

To show the suitability for the process to be carried out at very high pressures, the following experiments were conducted. 2.1 Grams of 2,5-Dimethyl furan ("DMF") was subjected to contact with ethylene in the presence of acetic acid ("AcOH") and acetic anhydride ("AcOAc") at different temperatures for six or four hours. The reactor pressure was kept constant at the values indicated in Table 8. The product obtained was p-xylene ("pXy"). In experiment No. 60 the reactor was also supplied with an amount of an antioxidant (butyl-hydroxytoluene) in an amount of about 10% wt based on the DMF. Other reaction conditions and yields are shown in Table 8.

TABLE 8

| Exp. No. | T, ° C. | P, bar | Time, hr | AcOH, g | AcOAc, g | Yield pXy, % |
| --- | --- | --- | --- | --- | --- | --- |
| 60 | 200 | 761 | 4.0 | 8.0 | 4.5 | 37.0 |
| 61 | 240 | 755 | 6.0 | 8.0 | 4.5 | 34.0 |

These results show that the process can be carried out at very high pressures. The presence of an antioxidant does not seem to make a significant difference.

Example 8

In order to show the influence of the presence of a desiccating agent during the reaction the following experiments were conducted. DMF (150 mg/mL) was contacted with ethylene at a pressure of about 84 bar at 280° C. for 4 or 8 hours in the presence of acetic acid ("AcOH"), acetic anhydride ("AcOAc") and/or benzoic anhydride ("BzOBz"). At the end of the reaction the conversion of DMF, the yield of p-xylene ("pXy") and the yield of 2,5-hexadione ("HDO") were determined. Reaction conditions and results are shown in Table 9.

TABLE 9

| Exp. No. | AcOH, mL | AcOAc, mL | BzOBz, g | Time, hr | Conversion, % | pXy, % | HDO, % |
| --- | --- | --- | --- | --- | --- | --- | --- |
| 62 | 1.0 | — | — | 4 | 80.4 | 68.5 | 12.1 |
| 63 | 0.75 | 0.25 | — | 4 | 93.8 | 17.6 | 0.5 |

TABLE 9-continued

| Exp. No. | AcOH, mL | AcOAc, mL | BzOBz, g | Time, hr | Conversion, % | pXy, % | HDO, % |
|---|---|---|---|---|---|---|---|
| 64 | 1.0 | — | 0.5 | 4 | 83.5 | 79.0 | 1.1 |
| 65 | 1.0 | — | — | 8 | 96.7 | 78.3 | 1.9 |
| 66 | 0.75 | 0.25 | — | 8 | 94.7 | 58.2 | 0.7 |
| 67 | 1.0 | — | 0.5 | 8 | 98.0 | 92.3 | 0.0 |

These results clearly show that excellent results are obtainable with reaction systems that do not contain a desiccating agent. When they do contain a desiccating agent it appears that benzoic anhydride is particularly suitable.

The invention claimed is:

1. A process for the preparation of benzene derivatives of the formula (I);

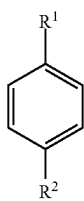
(I)

wherein $R^1$ and $R^2$, are the same or different and independently are selected from the group consisting of hydrogen, alkyl, aralkyl, —CHO, —CH$_2$OR$^3$, —CH(OR$^4$)(OR$^5$) and —COOR$^6$, wherein $R^3$, $R^4$ and $R^5$ are the same or different and are selected from hydrogen, alkyl, aryl, alkaryl, aralkyl, alkylcarbonyl or arylcarbonyl, or wherein $R^4$ and $R^5$ together form an alkylene group and wherein $R^6$ is selected from hydrogen, alkyl and aryl, which process comprises:
reacting a furan derivative of formula (II):

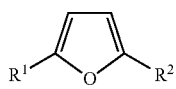
(II)

wherein $R^1$ and $R^2$ have the meanings above,
with ethylene under cycloaddition reaction conditions to produce the benzene derivative, wherein the reaction of the furan derivative and ethylene is carried out in the presence of an acid solvent, and the acid solvent is a carboxylic acid and is present in a weight ratio acid solvent to furan derivative from 1:1 to 250:1.

2. The process according to claim 1, wherein $R^1$ and $R^2$ independently comprise 1 to 8 carbon atoms, optionally in addition to one or more oxygen atoms.

3. The process according to claim 1, wherein at least one of $R^1$ and $R^2$ is alkyl, and wherein the alkyl comprises from 1 to 6 carbon atoms.

4. The process according to claim 1, wherein at least one of $R^1$ and $R^2$ is a —COOR$^6$ group.

5. The process according to claim 1, wherein $R^3$, $R^4$, $R^5$ and $R^6$ independently comprise from 1 to 7 carbon atoms.

6. The process according to claim 1, wherein a desiccating agent is present.

7. The process according to claim 6, wherein the amount of desiccating agent is in the range of from 50 to 1000% wt, based on the amount of furan derivative.

8. The process according to claim 6, wherein the desiccating agent is an organic desiccating agent.

9. The process according to claim 8, wherein the organic desiccating agent is a carboxylic acid anhydride.

10. The process according to claim 9, wherein the number of carbon atoms in the carboxylic acid anhydride ranges from 2 to 18 carbon atoms.

11. The process according to claim 9, wherein the carboxylic acid anhydride is acetic anhydride, benzoic anhydride or a mixture thereof.

12. The process according to claim 1, wherein further an additional dehydration catalyst is present.

13. The process according to claim 12, wherein the additional dehydration catalyst is a Diels Alder catalyst.

14. The process according to claim 12, wherein the additional dehydration catalyst has been selected from Lewis acids, Brønsted acids, activated carbon, silica, alumina, silica-alumina, zirconia, zeolites and mixtures thereof.

15. The process according to claim 12, wherein the additional dehydration catalyst comprises carbon, silica, alumina, silica-alumina, zirconia and/or zeolites as support for a catalytically active metal or metal compound.

16. The process according to claim 14, wherein the additional dehydration catalyst is an organic or inorganic Brønsted acid.

17. The process according to claim 6, wherein the desiccating agent is a carboxylic acid anhydride and the acid solvent is the carboxylic acid derived from this carboxylic acid anhydride.

18. The process according to claim 12, wherein the amount of additional dehydration catalyst is at least 0.5% wt.

19. The process according to claim 1, wherein the acid solvent comprises a carboxylic acid that contains 1 to 16 carbon atoms.

20. The process according to claim 19, wherein the acid solvent comprises a carboxylic acid that is used as dehydrating agent.

21. The process according to claim 1, wherein an additional solvent is included in the mixture of furan derivative, ethylene, acid solvent and optionally desiccating agent.

22. The process according to claim 21, wherein the solvent is selected from the group consisting of water, alcohols, esters, ketones, amides, aldehydes, acids, ethers, aliphatic or aromatic hydrocarbons, ionic liquids and sulphoxides.

23. The process according to claim 1, wherein the furan derivative of formula (II) is reacted with ethylene at a temperature in the range from 100 to 450° C.

24. The process according to claim 1, wherein the furan derivative of formula (II) is reacted with ethylene at an ethylene partial pressure of 10 bar to 1000 bar.

25. The process according to claim 1, wherein the furan derivative of formula (II) is reacted with ethylene for 0.5 to 72 hours.

26. The process according to claim 1, wherein $R^1$ and $R^2$ are the same or different and independently are selected from the group consisting of alkyl, —CHO, —CH$_2$OR$^3$ and —CH(OR$^4$)(OR$^5$), wherein $R^3$, $R^4$ and $R^5$ are the same or different and are selected from hydrogen, alkyl, aryl, alkylcarbonyl or arylcarbonyl, or wherein $R^4$ and $R^5$ together form an alkylene group, which process further comprises the steps of:

recovering a para-substituted benzene derivative product of the reaction between the furan derivative of formula (II) and ethylene; and oxidizing the thus obtained para-substituted benzene derivative product to yield terephthalic acid.

27. The process according to claim 26, wherein the oxidizing of the para-substituted benzene derivative product is effected by an oxygen-containing gas in the presence of a catalyst comprising cobalt and manganese.

28. The process according to claim 27, wherein the catalyst further comprises bromine.

29. The process according to claim 26, wherein the oxidizing is carried out at a temperature of from 60 to 220° C., at a pressure of from 5 to 100 bar and at a residence time of from 0.1 to 48 hours.

30. The process according to claim 3, wherein the alkyl is methyl or ethyl.

31. The process according to claim 5, wherein $R^3$, $R^4$, $R^5$ and $R^6$ independently comprise from 1 to 4 carbon atoms.

32. The process according to claim 10, wherein the number of carbon atoms in the carboxylic acid anhydride ranges from 2 to 8 carbon atoms.

33. The process according to claim 15, wherein the catalytically active metal or metal compound includes alkali metals, alkaline earth metals, transition metals, noble metals, rare earth metals or mixtures thereof.

34. The process according to claim 19, wherein the acid solvent comprises a carboxylic acid that contains from 1 to 8 carbon atoms.

* * * * *